United States Patent [19]
Natori

[11] Patent Number: 6,124,447
[45] Date of Patent: Sep. 26, 2000

[54] ENZYME CATALYZING DEPHOSPHORYLATION

[75] Inventor: Shunji Natori, Tone-Machi, Japan

[73] Assignee: The University of Tokyo, Tokyo, Japan

[21] Appl. No.: 09/121,964

[22] Filed: Jul. 24, 1998

[30] Foreign Application Priority Data

Nov. 20, 1997 [JP] Japan ................................. 9-319635

[51] Int. Cl.$^7$ ........................... C07H 21/04; C12P 21/06; C12N 9/14; C12N 1/20; C12N 15/00

[52] U.S. Cl. ........................ 536/23.2; 435/195; 435/196; 435/252.3; 435/320.1; 435/69.1; 530/350

[58] Field of Search ........................... 536/23.2; 435/69.1, 435/195, 196, 252.3, 320.1; 530/350

[56] References Cited

U.S. PATENT DOCUMENTS 5,106,735  4/1992  Natori et al. ........................... 435/91

*Primary Examiner*—Ponnathapu Achutamurthy
*Assistant Examiner*—Tekchand Saidha
*Attorney, Agent, or Firm*—Venable; John W. Schneller

[57] ABSTRACT

There are provided a protein having an action as a substrate protein of cathepsin L and having an amino acid sequence shown by SEQ ID NO: 1 of the Sequence Listing, an enzyme comprising the same which catalyzes dephosphorylation and an antibody to the protein. The present invention relates to a protein having an action as a substrate protein of cathepsin L and having an amino acid sequence shown by SEQ ID NO: 1 of the Sequence Listing, and enzyme comprising the same which catalyzes dephosphorylation and an antibody to the protein.

1 Claim, 4 Drawing Sheets

FIG_1

FIG_2

FIG_3

E64 insectsaline no treatment benzamizine

| | |
|---|---|
| hIA-2 | VHCSDGAGRTGTY |
| hPTN3 | VHCSAGIGRTGVL |
| dPTP | VHCSAGVGRTGTL |
| rOSTP | VHCSAGVGRTGTF |
| C.e | VHCSDGWDRTTQV |
| S.c | VHCSDGWDRTSQV |
| MIT1 | VHCSDGWDRTAQL |
| 100kDa | IHCISGWDRTPLF |

```
         .**  .*****.
```

ENZYME CATALYZING DEPHOSPHORYLATION

BACKGROUND OF THE INVENTION

1. Field of the invention

This invention relates to a novel enzyme which catalyzes a dephosphorylation and protein. The protein having an enzyme activity of the present invention supplies a phosphoric acid which is particularly necessary for of an oosperm at a growing period thereof and is a substance capable of exterminating injurious insects by inhibiting a growth effect of the oosperm or an activity thereof.

2. Prior art

Biology has made remarkable progress of late. As a result, various molecules explaining morphogenesis have been identified as of today. There have been known growth factors which drastically induce morphogenesis, adhesion factors which mediate between cells, and the like.

However, there are many morphologies of differentiation which cannot be explained by the known growth factors or adhesion factors. Among these, researches on protease which take notice of development have scarcely been carried out so that the present inventor aimed the function of protease at the development process. Protease can make reaction irreversible by decomposing a protein so that it can be considered that it would be inevitable for development of an organism having a property of channeling or direction. Thus, it can be considered that if the function of the protease at the development stage can be clarified, a novel viewpoint can be obtained for understanding the development.

Up to this day, as a protease which participates in the development, *Sarcophaga peregrina* cathepsin L has been found. The *sarcophaga peregrina* cathepsin L is shown to be essential for morphogenesis at metamorphosis stage of complete metamorphosis insects. In the complete metamorphosis insects, there exists. The imaginal disk is existing in a larva body and differentiated to an imago tissue by stimulation of ecdysone which is a metamorphosis hormone at the period of chrysalis.

It has been known that an imaginal disk was extracted from a larva body and morphogenesis to an imago tissue can be reproduced in an in vitro culture system in which the imaginal disk cultured in the presence of ecdysone. There has been also reported by using the above culture system that it is essential for differentiate the imaginal disk to an imago leg to secrete cathepsin L out of cells by the induction of ecdysone and to decompose a protein on a basement membrane of the imaginal disk. This demonstrates that intracellular lysosome enzyme cathepsin L has an important function in morphogenesis in addition to the function of decomposing an unnecessary protein in a cell.

The action of cathepsin L at metamorphosis stage has now been elucidated with a certain extent but the action of cathepsin at a development stage other than the metamorphosis stage has not yet been known. It is important to elucidate the function of cathepsin L at the development stage since it makes possible to control development by promoting of inhibiting et al. Thus, the present inventor has analyzed gene expression and protein expression of cathepsin L.

Figure 1:
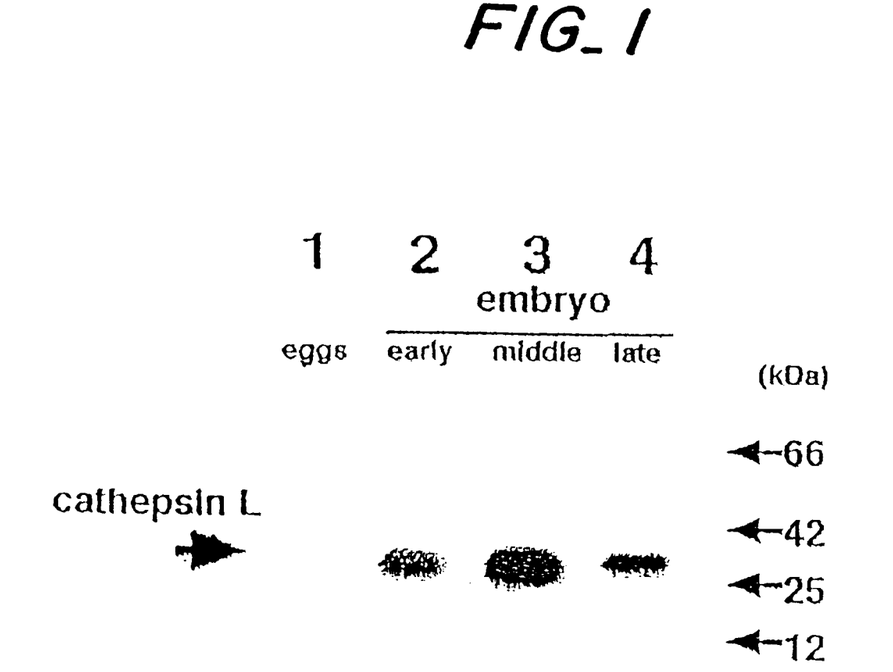
FIG. 1 is a drawing showing an immunoblotting of cathepsin L in a fertilized egg and a non-fertilized egg.

As a result, I have obtained an interesting knowledge particularly at the initial stage of embryogenesis. It has been clarified that cathepsin L exists as maternal mRNA and a precursor protein in a non-fertilized egg and exists as a matured protein from the initial stage of embryogenesis. That is, with regard to fertilized eggs and non-fertilized eggs of *sarcophaga peregrina* (Non-fertilized eggs are collected by separating imagoes immediately after eclosion to male and female, grown in separate cages and collected from abdomen of female after 5 days from eclosion using a pincette in an insect saline. Fertilized eggs are collected from female which is bred in a cage simultaneously with male. After eclosion, embryo at the fifth day is called as "early", at the 7th days as "middle" and at the 9th days as "late".), presence of cathepsin L is tested. The results are shown in FIG. 1. In FIG. 1, 50 µg of homogenate protein is used in respective lanes, and Lane 1 shows a non-fertilized egg, Lane 2 early egg embryo, Lane 3 middle egg embryo and Lane 4 late egg embryo. An arrow shows the position of a matured type cathepsin L (35 kDa). As can be clearly seen from Lanes 1 and 2 in FIG. 1, the presence of a matured type cathepsin L is confirmed from early embryo.

Early embryogenesis of complete metamorphosis insects may look like different from the other organisms. At the early stage of embryogenesis, however, embryo has not yet differentiated to the respective tissues and many reserved life phenomena which are similar to the other species can be found. For example, determination of dorso-ventical axis is made by a concentration gradient of a growth factor along with the body axis, and it has been reported that it is completely the same mechanism between drosophila (fruit fly) and African clawed toad.

Accordingly, if the function of cathepsin L can be clarified at the early embryogenesis, there is a great possibility of showing the function of protease common in embryogenesis not only in insects, but also in a common organisms.

From the above fact, the present inventor has conducted identification of an intravital substrate at the early embryogenesis was subjected to cloning to clarify an important function of cathepsin L at the early embryogenesis which can be considered to be common to a living body. It has also been desired to prepare an antibody to the protein.

The present inventor tried to identify an intravital substrate at the early embryogenesis to clarify the function of cathepsin L in the early embryogenesis. And analysis of localization of a substrate protein and cloning of cDNA are carried out as mentioned below.

(1) A protein with a molecular weight of 100 kDa on SDS-PAGE which can be considered to be an intravital substrate of cathepsin L at the early embryogenesis in a non-fertilized egg homogenated protein is determined.

(2) From the analysis of localization in the early embryo, it is found that the 100 kDa protein exists at the center portion of embryo in which cells have not yet been formed and cathepsin L is similarly localized.

(3) By cloning of cDNA which encodes the 100 kDa protein, the 100 kDa protein is found to be a novel protein.

(4) An antibody to the 100 kDa protein is prepared.

SUMMARY OF THE INVENTION

That is, the present invention relates to a protein with 100 kDa having an action as a substrate protein of cathepsin L and having an amino acid sequence shown by SEQ ID. NO: 1 of the Sequence Listing and also the invention relates to DNA having a base sequence encoding the same.

he present invention also relates to an enzyme which catalyzes a dephosphorylation comprising a protein having an amino acid sequence shown by SEQ ID. NO: 1 of the Sequence Listing which is obtained by analyzing the function possessed by the said protein with 100 kDa.

The present invention further relates to an antibody to the above-mentioned protein with 100 kDa.

BRIEF DESCRIPTION OF THE DRAWINGS

FIG. 4 is a graph showing the results of FIG. 3 as a function of

DESCRIPTION OF THE PREFERRED EMBODIMENTS

The protein of the present invention is explained below.

An intravital substrate of cathepsin L was identified by homogenizing non-fertilized eggs of *sarcophaga peregrina*, adding a purified cathepsin L thereto, incubating and detecting a protein which disappears by SDS-PAGE. As the result, the protein with a molecular weight of 100 kDa on SDS-PAGE was disappeared depending on the amount of the purified cathepsin L added. This protein with about 100 kDa was also disappeared in the stage of actual embryogenesis. From the above facts, the protein with a molecular weight of about 100 kDa was made a candidate of an intravital substrate of cathepsin L.

To confirm that the 100 kDa protein disappears in the actual embryogenesis, manifestation of the 100 kDa protein at embryogenesis was analyzed by an immunoblotting method. For this purpose, an antibody to the 100 kDa protein is firstly prepared. That is, non-fertilized egg homogenated protein was subjected to SDS-PAGE, the portion corresponding to 100 kDa protein was cut off from a gel to perform SDS-urea PAGE. Then, a single band was cut from the gel, immuno-sensitized to a rabbit to obtain an antiserum, and the antiserum was subjected to affinity purification to obtain an anti- 100 kDa antibody.

By using the thus obtained antibody, an immunoblotting analysis was carried out to embryo homogenates at the respective embryogenesis stage. As the result, it was found that almost all the portions of the 100 kDa protein was decomposed at the early embryogenesis and completely decomposed after the middle stage (see FIG. 2).

Figure 2:
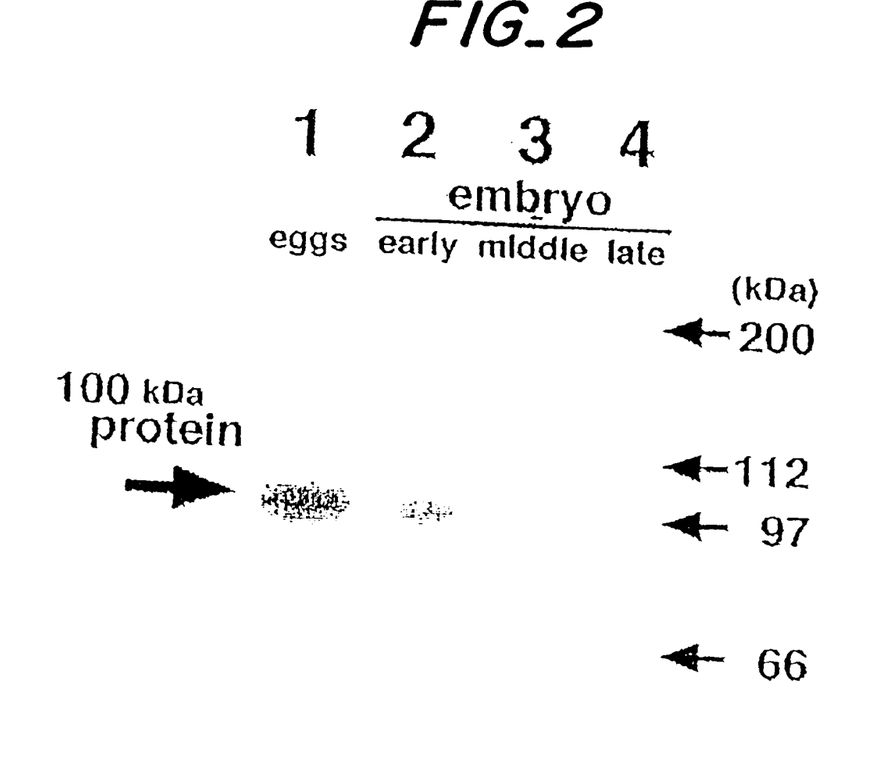
FIG. 2 is a drawing showing an immunoblotting of a protein with 100 kDa in a fertilized egg and a non-fertilized egg.

In FIG. 2, each 10 μg of embryos of non-fertilized eggs and fertilized eggs at the respective stage was used. Lane 1 shows non-fertilized eggs, Lane 2 the early embryo, Lane 3 the middle embryo, Lane 4 the late embryo, and an arrow shows the position of the 100 kDa protein. As can be clearly seen from Lane 1 and Lane 2, it can be confirmed that the 100 kDa protein existing in the non-fertilized egg almost disappeared at the early stage in the actual embryogenesis.

From the above facts, the protein having a molecular weight of about 100 kDa which is (a) a protein disappearing on SDS-PAGE by treating a purified cathepsin L, and (b) a protein disappearing at the early embryogenesis could be identified.

It is the problem whether cathepsin L hydrolyses the 100 kDa protein as an intravital substrate in vivo or not.

Thus, to examine whether the 100 kDa protein was an intravital substrate of cathepsin L or not, a cysteine protease inhibitor E64 was injected to embryo of *sarcophaga peregrina* at the early stage. As the result, it was found that a rate of hydrolysis of the 100 kDa protein became late in the embryo to which E64 was injected, as compared to that in the embryo to which a serine protease inhibitor, namely benzamizine, and that in the non-treated embryo (see FIG. 3).

Figure 3:
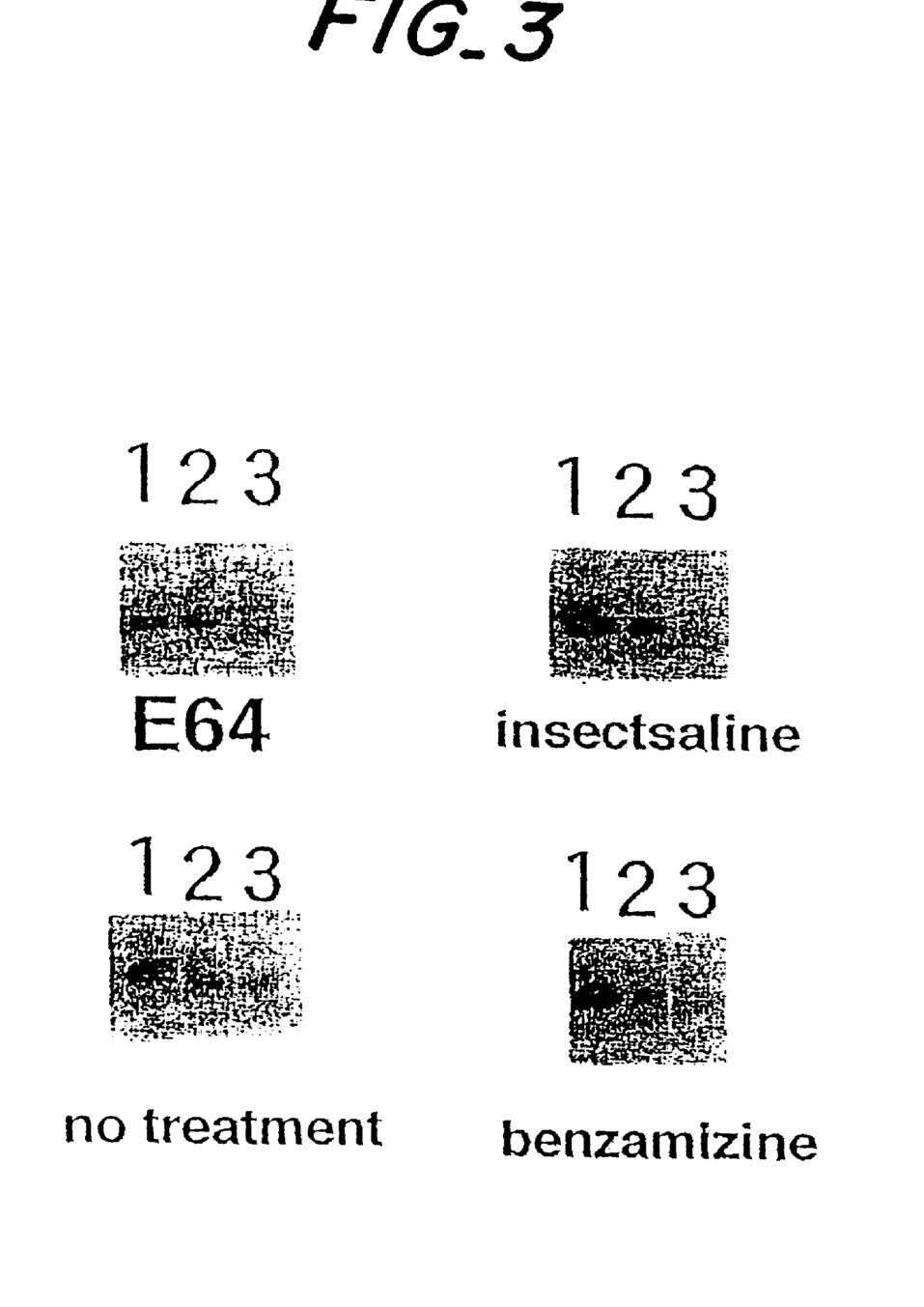
FIG. 3 is a drawing showing inhibition of proteolysis of a protein with 100 kDa in vivo by E64, etc.
Figure 4:
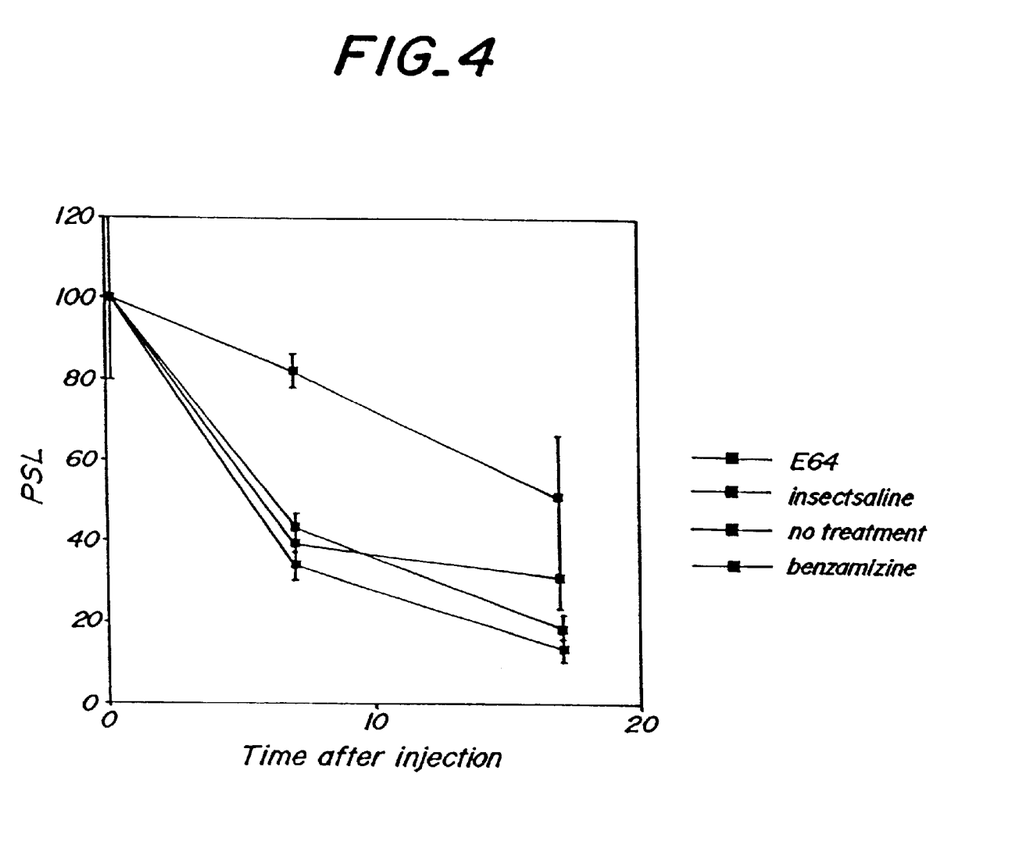

That is, in the experiment shown in FIG. 3, a cysteine protease inhibitor E64, insect saline, and a serine protease inhibitor, benzamizine were each injected to embryo of *sarcophaga peregrina* at the early stage, and the embryos were recovered at 0 hour, after 7 hours and 17 hours. Thereafter, an embryo of each fly was homogenized and whether decomposition of the 100 kDa protein was inhibited or not was examined by the immunoblotting. Three samples were checked with respect to each point of time. Lane 1 is the sample at 0 hour after injection, Lane 2 after 7 hours and Lane 3 after 17 hours. In FIG. 3, left upper drawing is in the case of E64, right upper drawing is in the case of insect saline, left lower drawing is a non-treated case, and right lower drawing is in the case of benzamizine. FIG. 4 shows quantitative analysis values obtained in the experiments shown in FIG. 3 by using an image analyzer. The obtained value of the sample at 0 hour is made 100%. Error bars show the standard deviation of the measured values of three samples.

These results strongly suggests that the 100 kDa protein is an intravital substrate of cathepsin L.

Next, analysis of localization and cloning of cDNA were carried out to know the function of the 100 kDa protein identified by the present inventor on early embryogenesis.

A frozen slice of an early embryo of *sarcophaga peregrina* was prepared and a fluorescent antibody method was performed by using an anti-100 kDa antibody to know localization of the substrate protein. As the result, fluorescence was detected all over the center portion of the embryo (Figure not shown). At the center portion of the embryo at this stage, cells are not yet formed. On the other hand, when localization of cathepsin L was analyzed in the same fluorescent antibody method, fluorescence was observed in the cells and also fluorescence was observed all over the center portion of the embryo as in the localization of 100 kDa. From the above facts, it can be considered that the 100 kDa protein would be hydrolyzed by cathepsin L existing over the center portion of the embryo prior to forming cells. This results do not contradict to the matter that the 100 kDa protein is an intravital substrate of cathepsin L. Also, this protein can be considered to be a protein contained in granules of a yolk.

On the other hand, lysosome enzyme cathepsin L is an intracellular small organ lysosome and has been considered to have a function of decomposing unnecessary proteins. Also, cathepsin L functions in a lysosome, and cells secrete cathepsin L in the course of morphogenesis of imaginal disk. It is shown to be essential to decompose a protein on a basement membrane. It can be now found that cathepsin L already exists in early embryogenesis before forming cells. From this fact, it can be considered to be important that cathepsin L is prepared at the center portion of embryo in early embryogenesis before forming cells and the protein is decomposed therein.

Moreover, fluorescence caused by the 100 kDa protein and cathepsin L was detected from whole portion of the non-fertilized egg by the fluorescence antibody method, so that it is suggested that they exist in the whole portion of the non-fertilized egg.

Next, cloning of cDNA was carried out to know the true nature of the 100 kDa protein.

To obtain cDNA which encodes the 100 kDa protein, a total RNA was firstly obtained from ovary of *sarcophaga*

*peregrina* to prepare a cDNA library (ZAP-cDNA synthesis kit of stratagene was used). Then, immunoscreening was performed to the library by using an antibody to the 100 kDa protein. As the result, 22 positive clones were obtained from 36,000 clones. When Southern blotting hybridization was performed to the resulting positive clones with a nucleic acid sequence expected from a partial amino acid sequence already determined as a probe, signals were observed in 13 clones. These clones were analyzed and found that one of which had an open reading frame which encodes 724 amino acids and contained five parts of amino acid sequences previously determined (see an amino acid sequence of SEQ ID NO: 1 of the Sequence Listing). From the above, it is concluded that the clone is cDNA of the 100 kDa protein.

An amino acid sequence of the protein with about 100 kDa of the present invention and a base sequence encoding the same are shown in SEQ ID NO: 1 and NO: 2 of the Sequence Listing, respectively.

Homology search was conducted by using the whole length of the amino acid sequence of this 100 kDa protein to the already existing data base but no homologous showing significance can be found out.

However, the middle portion of the 100 kDa protein showed a high homology with a protein belonging to myotubularin-related family which is considered to be tyrosine-phosphatase as shown in SEQ ID NO8 and SEQ ID NO: 9.

SEQ ID NO: 8 shows an amino acid sequence of human myotubularin in comparison with 100 kDa protein and homologue thereof.

SEQ ID NO: 9 shows an amino acid sequence of C. elegance myotubularin.

Figure 5:
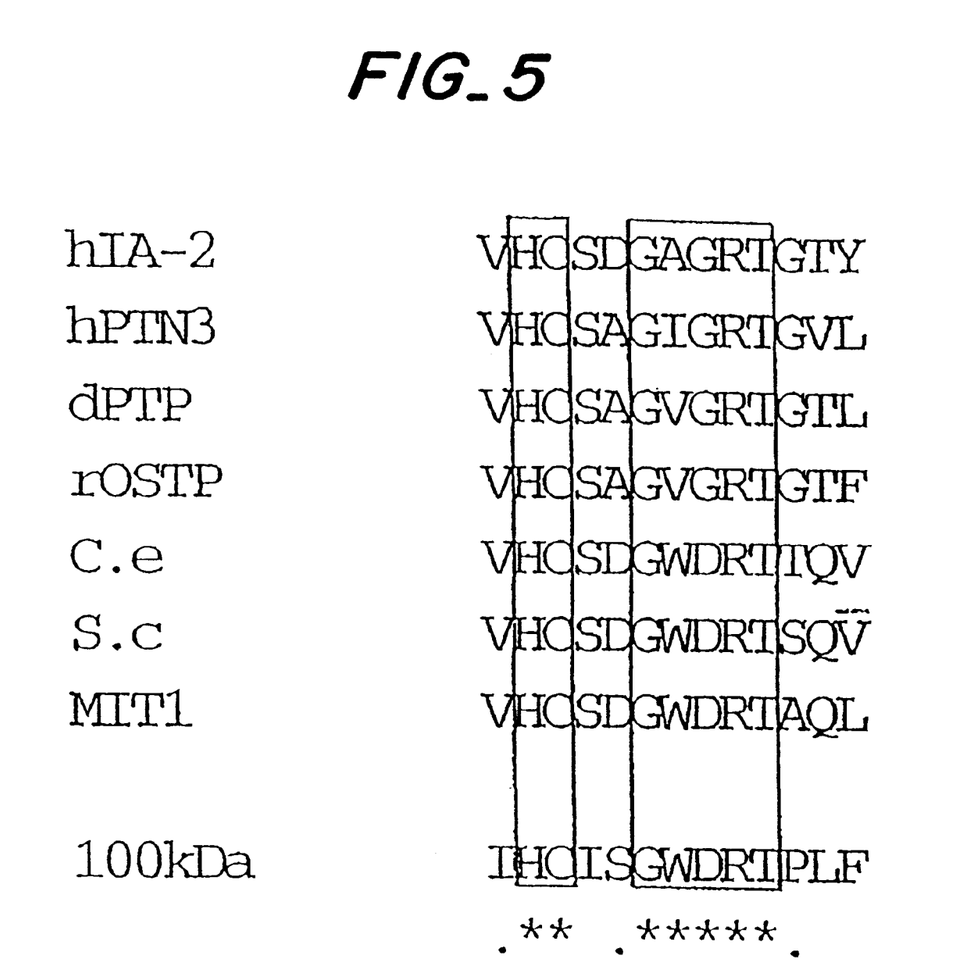
FIG. 5 shown a comparison of amino acid sequences between 100 kDa protein and other protein.

Both of lower lines in SEQ ID NO: 8 and SEQ ID NO: 9 show amino acid sequences of the 100 kDa protein. Asterisks mean a coincident amino acid and dots mean an amino acid having similar characteristics. The numeral at the left end shows the position from the first methionine. A sequence preserved in tyrosine phosphatase is underlined. The sequence showed 22% homology with 135 amino acids of myotubularin-like protein of *C. elegance* and 32% homology with 69 amino acids of human myotubularin. And yet, the sequence contained 13 amino acids which are well preserved in thyrosine-phosphatase therebetween. Cysteine which is considered to be necessary for an activity is also preserved (FIG. 5). In FIG. 5, asterisks mean a coincident amino acid and dots mean an amino acid having similar characteristics. hIA-2 in FIG. 5 shows human receptor-type partial amino acid sequence, hPTN3 human intracellular type partial amino acid sequence, dPTP Drosophila receptor-type partial amino acid sequence, rOSTP rat receptor-type partial amino acid sequence, *C.e. C. elegans* partial amino acid sequence, and *S.c. S. cerevisiae* partial amino acid sequence, respectively. From the above facts, the 100 kDa protein can be considered to be thyrosine-phosphatase. An interesting point is that there is no homology in the preserved amino acid sequences at the N-terminal side and the C-terminal side.

In addition, as a motif structure, there exist 11 portions of N-type sugar chain addition site. There is no sequence which is considered to be a signal sequence or a transmembrane domain.

In addition, the 100 kDa protein is a serine-enriched protein (12% of the whole), especially serine exists mainly at the C-terminal side. Thyrosine is also enriched and the total amount of serine and thyrosine is about 20% of the whole amino acids. Many phosphated sites exist over the whole sequence.

According to the above, it can be clarified that the 100 kDa protein is structurally novel protein.

Next, the function of the 100 kDa protein of the present invention is investigated.

If the 100 kDa protein is phosphatase, it would release a phosphoric acid by its dephosphorylation activity to supply a phosphoric acid necessary for early embryogenesis in view of the fact that many phosphated sites exist in the 100 kDa protein. In embryogenesis at the early stage, a large amount of polyphosphoric acid exists. A phosphoric acid at early embryogenesis may be supplied by subjecting the 100 kDa protein to dephosphorylation from the polyphosphoric acid.

The present inventor tried to identify an intravital substrate in early embryogenesis to clarify the function of cathepsin L in early embryogenesis, and the protein with a molecular weight of 100 kDa on SDS-PAGE is identified as an intravital substrate. There is substantially no example which identifies the substrate of protease in early embryogenesis by not using genetic means but biochemical means.

Next, from the analytical result of localization in embryo at the early stage by an indirect fluorescence antibody method, it can be found that the 100 kDa protein is localized as in the embryo in which no cell has been formed. It can be also found that cathepsin L exists at the center portion of embryo at early embryogenesis. From the above facts, it can be considered that lysosome enzyme cathepsin L is prepared at the center portion of embryo at early embryogenesis prior to formation of cells and it may be important to decompose the protein at the portion. Also, this result suggests that cathepsin L exists in the 100 kDa protein.

According to cDNA cloning, the 100 kDa protein is a structurally novel protein and the middle portion showed a high homology as myotubularin which is considered to have thyrosine-phosphatase. From the above fact, there is a possibility that the 100 kDa protein is considered to be thyrosine-phosphatase.

According to the present invention, the function of the protein of the present invention at the early stage of a fertilized egg is clarified so that a substance which is available for controlling growth such as growth or inhibition of a fertilized egg and an antibody thereof are provided by the present invention.

EXAMPLES

In the following, the present invention is explained in more detail by referring to Examples, but the present invention is not limited by these Examples.

Example 1

Preparation of Experimental Animal

Imaginal of *sarcophaga peregrina* was bred at 27° C. Larvae were bred in a Tupperware always filling with water and end aged larvae were made chrysalis by drying with a dryer.

Non-fertilized eggs were collected by separating imagoes immediately after eclosion to male and female, grown in separate cages and collected from abdomen of female after 5 days from eclosion by a pincette in an insect saline.

Fertilized eggs are collected from female which is grown in a cage simultaneously with male. After eclosion, embryo at the fifth day is called as "early", at the 7th days as "middle" and at the 9th days as "late".

Example 2

Purification of 100 kDa Protein

Non-fertilized eggs of *sarcophaga peregrina* were homogenized with a 50 mM Na-phosphate buffer (pH 5.8), 500 μg of protein was subjected to SDS-PAGE and after CBB staining, the portion corresponding to 100 kDa protein was cut out from a gel. When the cut out gel was substituted with a SDS sample buffer for 4 hours, then SDS-urea PAGE was performed, a single band and a broad band were detected. A recovered rate of the single band was estimated to be 60% or more from the comparison with a molecular weight marker and CBB staining strength. Also, this band was decreased depending on embryogenesis on SDS-urea PAGE. From the above procedure, the 100 kDa protein was judged to be purified. In the following, the single band on SDS-urea PAGE is treated as the 100 kDa protein.

Example 3

Preparation of Anti 100 kDa Antibody

15 μg of the 100 kDa protein purified by the two-dimensional electrophoresis (the first dimension; SDS-PAGE, the second dimension; SDS-urea PAGE) was homogenized in 0.5 ml of PBS, suspended with an equal amount of an adjuvant and the mixture was made an emulsion by an ultrasonic wave to prepare an immuno antigen for one use. A complete adjuvant was used only for the first sensitization and an incomplete adjuvant was used after the second sensitization.

It was sensitized to a female albino rabbit four times with an interval of every one week. Blood was collected from ear vein and allowed to stand at 37° C. for one hour, and then allowed to stand at 4° C. overnight to obtain serum from supernatant.

Example 4

Purification of Affinity of Antibody

The 100 kDa protein (50 μg) subjected to SDS-urea PAGE was transferred to a PVDF membrane to cut out the objective band. This was subjected to blocking by a skim milk sol (20 mM Tris/HCl, pH=7.9, 5% skim milk) and after reacting it with 10 ml of antiserum for 4 hours, 200 mM of glycine/HCl (pH=2.8) was added to extract an antibody. The extract was neutralized with 1M KOH.

Example 5 (Preparation of cDNA library of sarcophaga peregrina ovary (followed by protocol of stratagene))

According to the guanidine hot phenol method, whole RNA of sarcophaga peregrina (egg maturation late) was obtained. Migrated genome was removed from 300 μg of whole RNA by CsCl ultracentrifugation with 230,000 g at 20° C. for 12 hours, and 10 μg of a poly(A)mRNA was purified by using oligotex-dT30. Purified 5 μg of the poly (A)mRNA was used for preparing a cDNA library. For preparation of cDNA library, ZAP-cDNA synthesis kit (stratagene) was used. As the result, a cDNA library with a library size of $3.9 \times 10^5$ (390,000) pfu was structured.

Example 6

Immunoscreening Using an Antibody

Phage cDNA library was infected to an E. coli (XL1-blue MRF') and seeded on a NZY plate. After culturing at 42° C. for 3.5 hours, the protein was induced at 37° C. overnight by 20 mM of IPTG-treated nitrocellulose filter, and the nitrocellulose filter adsorbed a protein was subjected to blocking with a 3% gelatin solution. Next, an anti 100 kDa antibody (4 μg/ml) purified by affinity was reacted at 27° C. for 2 hours, and reacted with an anti-rabbit IgG antibody to which an alkali phosphatase is conjugated at 27° C. for 2 hours. Then, by a coloration reaction of alkali phosphatase, a positive plaque was detected.

Example 7

Determination of Partial Amino Acid Sequence of 100 kDa Protein

A non-fertilized egg homogenate (50 μg) was subjected to SDS-PAGE, and then, the position corresponding to the 100 kDa protein was cut out from the gel and subjected to SDS-urea PAGE. The gel was transferred to a nitrocellulose filter, stained by ponceau S and cut out the 100 kDa corresponding portion by a razor. Then, it is decolorized by 0.2 mM NaOH, treated by 0.5% PVP, added a 1/100 amount of lysyl end peptidase (in case of trypsine, a 1/10 amount was added) to the mixture and subjected to decolorization reaction under the conditions of 100 mM $NH_4HCO_3$ (pH=8) at 37° C. for 15 hours. The decomposed product was applied to C18HPLC and eluted by the gradient of 1%/min from H2O to acetonitrile in the presence of 0.05% TFA to fractionate peaks. The respective peaks were dried by a centrifugal evaporator and the sequences were determined by an automatic peptide sequencer.

The determined sequences are as follows. Treated by lysyl end peptidase

SEQ ID NO: 3 Phe Met Ala Val Ser Ser/Met Ser/Ala

SEQ ID NO: 4 Asp Leu His Asp Leu Leu Glu Phe Ile Phe Glu Lys

Treated by trypsine

SEQ ID NO: 5 Ile Phe Ile Gln Tyr Gly Lys

SEQ ID NO: 6 Phe Asn Asp Ala Leu Val Pro

SEQ ID NO: 7 Ala Val Pro Val Thr Met Tyr

Example 8

Fluorescent Antibody Method

From an early embryo collected from abdomen of imaginal female, cut pieces were prepared each 10 μm, fixed by 1.5% HCHO, and blocked by 1% FCS/TBS. They were reacted with a primary antibody diluted to 1/20 to 1/100 for one hour, then reacted with a FITC conjugated secondary antibody and 100 ng of DAPI for 30 minutes, encapsulated by 2.5% DABC 0.50% glycerol and observed by a fluorescent microscope.

What is claimed is:

1. An isolated DNA having a nucleic acid sequence shown by SEQ ID NO: 2 of the Sequence Listing.

* * * * *

SEQUENCE LISTING

<160> NUMBER OF SEQ ID NOS: 9

<210> SEQ ID NO 1
<211> LENGTH: 724
<212> TYPE: PRT
<213> ORGANISM: Sarcophaga peregrina

<400> SEQUENCE: 1

```
Met Ser Thr Thr Ile Glu Val Thr Gln Lys Asp Leu His Asp Leu Leu
  1               5                  10                  15

Glu Ile Phe Glu Lys Lys Pro Phe Asp Ala Gly Ser Cys Glu Lys Gly
             20                  25                  30

Ser Leu Glu Glu Asp Ile Thr Asn Arg Cys Glu Phe Leu Phe Lys Lys
         35                  40                  45

Asp Tyr Thr Leu Ile Glu Leu Asp Asn Ser Asn Gly Val Leu Ser Pro
     50                  55                  60

Arg Tyr Pro Gly Arg Ile Phe Ile Pro Glu Tyr Glu His Gly His Met
 65                  70                  75                  80

Thr Ser Thr Ile Thr Pro Asn Asn Thr Asn Leu Gly Thr Gln Ala Thr
                 85                  90                  95

Asn His Ala Ser Pro Gln Ser Gly Lys Asn Gly Asn Gly Leu Pro His
            100                 105                 110

Asn Pro Pro Ser Pro Ser Asn Ser Ile Ala Ser Asp Ser Thr Thr Pro
        115                 120                 125

Ser Thr Ser Ser Gly Ile Gln Ser Phe Val Thr Phe Ala Asn Ser Ala
    130                 135                 140

Thr Asn Asp Gln Gln Thr Ser Asn Pro Leu Tyr Asn Gln Asn Tyr Phe
145                 150                 155                 160

Pro Gln Leu Gln His Pro Ile Ala Ser Thr Ser Asn Ser Ile Ser Asn
                165                 170                 175

Asn Thr Ala Asn Asp Thr Ile Tyr Glu Asp Leu Tyr Asp Val Asn Lys
            180                 185                 190

Val Arg Glu Leu Ile Thr Met Ala Lys Tyr Ala Arg Cys Arg Gln Arg
        195                 200                 205

Phe Ala Val Pro Val Ile Met Tyr Arg Gly Lys Tyr Ile Cys Arg Ser
    210                 215                 220

Ala Thr Ile Ser Ile Asn Ala Glu Thr Tyr Gly Arg Lys Ala Val Asp
225                 230                 235                 240

Tyr Ala Tyr Asp Cys Ile Asn Gly Thr Asn Tyr Ser Glu Arg Ala Asn
                245                 250                 255

His Val Ala Asp Asp Glu Asn Asn Asp Asn Ser Glu Asp Ser Leu Met
            260                 265                 270

Asn Pro Pro Leu Asn Gly Gln Ser Gln Phe Ser Tyr Glu Glu Val Ile
        275                 280                 285

Lys Ser Asp Met Gln Leu Leu Asn Ser Leu Asn Val Thr Thr Ile Ile
    290                 295                 300

Asp Leu Met Val Glu Asn Arg Lys Ile Lys Tyr Phe Met Ala Val Ser
305                 310                 315                 320

Ser Ser Glu Lys Ala Asp Pro Glu Asn His Tyr Glu Ser Phe Asn Leu
                325                 330                 335

Val Ser Leu Pro Tyr Pro Gly Cys Glu Phe Lys Lys Phe Arg Asp
            340                 345                 350

Asn Asn Tyr Met Ala Glu Gly Leu His Tyr Asn Trp Lys Gln Ser Phe
```

```
                355                 360                 365
Asn Asp Ala Thr Leu Ser Val Pro Glu Ser Gly Pro Ala Arg Glu Leu
370                 375                 380

Asn Ile Asp Trp Ser Asp Tyr Lys Asn Trp Asp Leu Val Cys Ile Thr
385                 390                 395                 400

Gln Asn Tyr Val Lys Thr Cys Leu Lys Tyr Ile Lys Asp Glu Lys Ser
                405                 410                 415

Gly Leu Leu Ile His Cys Ile Ser Gly Trp Asp Arg Thr Pro Leu Phe
                420                 425                 430

Ile Ser Leu Ile Arg Leu Ser Leu Trp Ala Asp Gly Leu Ile His Gln
                435                 440                 445

Ser Leu Asn Pro Tyr Gln Met Thr Tyr Phe Thr Ile Ala Tyr Asp Trp
450                 455                 460

Tyr Leu Phe Gly His Gln Leu Pro Asp Arg Ile Lys Arg Gly Glu Asp
465                 470                 475                 480

Ile Met Phe Phe Cys Phe His Val Leu Lys Tyr Ile Met Gly Glu Glu
                485                 490                 495

Phe Ser Ile Ala Glu Gln Arg Arg Thr Lys Thr Ser Ser Ser Ser
                500                 505                 510

Gly Ser Ser Ile Val Val Leu Lys Cys Asp Ser Gly Asp Glu Ser Ala
                515                 520                 525

Ser Leu Lys Glu Ser Leu Leu Phe Asp Gln Asp Ser Asn Glu Ser Phe
530                 535                 540

Ser Asn Ser Ser Asn Cys Asp Asn Leu Pro Val Thr Asp Gly Tyr Tyr
545                 550                 555                 560

Ala Pro Val Thr Gly Pro Ser Thr Ser Thr Ala Thr Ala Gln Gly
                565                 570                 575

Ser Ser Val Ala Gly Asn Asn Pro Leu Thr Asn Arg Ser Pro Asn Leu
                580                 585                 590

Lys Arg Ser Lys Thr Ser Pro Ile Ser Val Pro Gly Ala Ser Ala Ala
                595                 600                 605

Arg Gln Arg His Glu Ser Tyr Ser Ser Thr Gly Gly Ser Trp Gln Val
                610                 615                 620

Val Thr Val Thr Gly Ser Ile Asp Ser Thr Asn Gly Ser Leu Thr Lys
625                 630                 635                 640

Arg Met Thr Glu Gln Arg Asp Asp Ser Asp Asn Arg Asp Thr Ser Asp
                645                 650                 655

Asn Gly Glu Asn Ser Gly Asn Asn Ser Ser Asn Thr Ala Ser Thr Ser
                660                 665                 670

Lys Glu Glu Glu Ser Ser Lys Pro Pro Asp Thr Pro Arg Met Gln
                675                 680                 685

Arg Leu Asn Ala Val Arg Ala Ile Phe Ile Gln Ser Tyr Gly Lys Gln
                690                 695                 700

Ile Gly Leu Lys Phe Lys Glu Gly Ser Ser Thr Asn Leu Ala Thr Leu
705                 710                 715                 720

Ile Gly Leu Arg

<210> SEQ ID NO 2
<211> LENGTH: 2707
<212> TYPE: DNA
<213> ORGANISM: Sarcophaga peregrina
<220> FEATURE:
<223> OTHER INFORMATION: "n" at various positions throughout the sequence may be
      A, T, C, G, other or unknown
```

-continued

```
<400> SEQUENCE: 2
ttcggcacga gcgtacataa aaagtagtac cgtttgcctg caattttgtg ataaaaaaaa    60
    aaaaaaaaac aattatcttt agtaaatcaa cgaaataaaa ttaataacta aaggcgtatc   120
    cataagcata agnatataat ttttgtacgt tgcataaata aatagtaaat gcatcgtcgt   180
    cgcaatgtcc acaacaatcg aagtgacgca gaaggatttg cacgatttgt tagaaatttt   240
    cgaaaaaaaa ccattcgatg ctggctcatg tgagaaaggg tcactggaag aagacataac   300
    gaatagatgt gaattcctat ttaaaaaaga ctatacacta attgaactcg ataatagcaa   360
    tggtgtctta agtccacgtt atccaggtcg aattttttata cccgaatacg aacatggcca   420
    tatgacatca accataacgc ccaataatac aaatttagga actcaagcaa caaaccatgc   480
    atcaccacag agtggtaaaa atggtaacgg tttacctcac aaccgccat caccatcgaa   540
    ttcaatagcg tctgatagta caacaccatc aactagtagt ggcataaat cgtttgtgac   600
    attcgccaat tcggcaacaa atgatcagca aactagcaat ccattatata atcaaaatta   660
    ttttccacaa ctacaacatc ccatagcatc gacatcaaat agtatcagca ataatacagc   720
    aaacgacacc atttacgaag acctctatga tgttaacaaa gtgcgagaac tcatcacaat   780
    ggccaaatat gcaagatgtc gccaacgttt cgctgttcct gttattatgt atcgtggcaa   840
    atacatttgc cgctcggcca ccatatccat caatgccgaa acgtatggtc gcaaagcagt   900
    tgattatgcc tatgactgca ttaatggcac aaactacagt gaacgggcaa atcatgttgc   960
    tgacgatgag aataatgata acagtgagga ttctttaatg aatccaccct taaacggcca  1020
    atcacagttc tcatacgaag aagttatcaa aagtgatatg caactgttga actccctaaa  1080
    cgttactaca atcatagatc taatggtaga gaatcgaaag attaaatatt ttatggctgt  1140
    ttcgtcatct gagaaagccg atcccgaaaa tcattatgaa agttttaatc tggtatcact  1200
    acctatcct ggctgtgaat tttttaagaa atttcgtgac aataattata tggcagaggg   1260
    attacattat aattggaaac aatcatttaa cgatgcaact ctaagtgtac ccgaatctgg  1320
    cccgcaaga gaactgaata tcgattggag tgattataaa aattgggatt tagtgtgcat  1380
    aacgcaaaat tacgtaaaga catgccttaa gtataaaa gatgagaaat caggtctatt  1440
    gattcactgt atcagtggct gggatcgtac gccattattt atatcactta tacgtttatc  1500
    tttgtgggct gatggtctta tacatcaatc gttaaatcct taccaaatga catattttac  1560
    aatagcttac gattggtatt tatttggtca tcagttgcca gatcgtataa aaagaggaga  1620
    agatattatg ttcttttgtt ttcatgtgct taaatatatt atgggcgaag aattttccat  1680
    tgcagagcaa agaagacgta ctaaaacatc gagtagtagt gggagtagta ttgttgttct  1740
    gaagtgtgat tccgcgatg agtcagcatc actgaaagaa tccctactat tcgatcaaga  1800
    cagcaatgaa agttttccaa atagttccaa ctgtgataat ttgcccgtaa cggatggtta  1860
    ctatgcgcct gtgaccgggc cctcaacgtc aacgacagca acagcacaag gtagtagtgt  1920
    agcgggaaat aatcctttaa caaatcgatc acctaaccta aaacgatcga aaactagtcc  1980
    catttctgtg ccaggtgcta gtgccgcacg tcagaggcat gaatcgtatt catcgaccgg  2040
    tggtagttgg caagtggtta ccgtaacggg ttcaattgat tccacgaatg gtagtttaac  2100
    aaagcgtatg acggaacagc gagacgacag cgataataga gacactagtg ataatggtga  2160
    aaacagtggt aacaaatagct caaatactgc cagtaccagt aaagaggagg agtcctcatc  2220
    aaaaccacca gatacaccgc gtatgcaacg tttaaatgct gttcgagcca tatttataca  2280
    gtcttatgga aaacaaattg gcctcaaatt taagaaggc tcttccacta atttagccac  2340
    acttattggt ttaaggtaaa aaagagagag aaaggagaga gagacgacaa aaaaaaaata  2400
    ttacaaacct tattaaaaat tttttttagt taagtgttcc attaaataaa ttctgatgat  2460
    gttctcttaa aatacttttta aactttgcat tgtaaactga aacgattata atattaactt  2520
    ttaattcgct atatacacca attttcgaat agatagatta ttaaatgatt atgtacaaca  2580
    agtaatatta tttgttttt atttcttcct ctataattat tgtattttcc ttttaagact  2640
    tcaaactata catacataca tactacccta ccctcaaacc cccctctccc taaatgccat  2700
    tagttat                                                             2707

<210> SEQ ID NO 3
<211> LENGTH: 7
<212> TYPE: PRT
<213> ORGANISM: Sarcophaga peregrina
<220> FEATURE:
<221> NAME/KEY: MOD_RES
<222> LOCATION: (6)
<223> OTHER INFORMATION: Ser or Met
<220> FEATURE:
<221> NAME/KEY: MOD_RES
<222> LOCATION: (7)
<223> OTHER INFORMATION: Ser or Ala

<400> SEQUENCE: 3

Phe Met Ala Val Ser Xaa Xaa
    1               5

<210> SEQ ID NO 4
<211> LENGTH: 12
<212> TYPE: PRT
<213> ORGANISM: Sarcophaga peregrina

<400> SEQUENCE: 4

Asp Leu His Asp Leu Leu Glu Phe Ile Phe Glu Lys
    1               5                   10
```

<210> SEQ ID NO 5
<211> LENGTH: 8
<212> TYPE: PRT
<213> ORGANISM: Sarcophaga peregrina

<400> SEQUENCE: 5

```
    Ile Phe Ile Gln Ser Tyr Gly Lys
     1               5
```

<210> SEQ ID NO 6
<211> LENGTH: 9
<212> TYPE: PRT
<213> ORGANISM: Sarcophaga peregrina

<400> SEQUENCE: 6

```
    Phe Asn Asp Ala Thr Leu Ser Val Pro
     1               5
```

<210> SEQ ID NO 7
<211> LENGTH: 7
<212> TYPE: PRT
<213> ORGANISM: Sarcophaga peregrina

<400> SEQUENCE: 7

```
    Ala Val Pro Val Thr Met Tyr
     1               5
```

<210> SEQ ID NO 8
<211> LENGTH: 621
<212> TYPE: PRT
<213> ORGANISM: Homo sapiens

<400> SEQUENCE: 8

```
    Ala Ala Glu Gln Pro Gly Asn Gly Gly Ala Arg Ser Pro Arg Val
     1               5                  10                  15
    Ser Arg Met Ala Ser Ala Ser Thr Ser Lys Tyr Asn Ser His Ser Leu
                    20                  25                  30
    Glu Asn Glu Ser Ile Lys Arg Thr Ser Arg Asp Gly Val Asn Arg Asp
                35                  40                  45
    Leu Thr Glu Ala Val Pro Arg Leu Pro Gly Leu Thr Leu Ile Thr Asp
        50                  55                  60
    Lys Glu Val Ile Tyr Ile Cys Pro Phe Asn Gly Pro Ile Lys Gly Arg
     65                  70                  75                  80
    Val Tyr Ile Thr Asn Tyr Arg Leu Tyr Leu Arg Ser Leu Glu Thr Asp
                    85                  90                  95
    Ser Ser Leu Ile Leu Asp Val Pro Leu Gly Val Ile Ser Arg Ile Glu
                100                 105                 110
    Lys Met Gly Gly Ala Thr Ser Arg Gly Glu Asn Ser Tyr Gly Leu Asp
                115                 120                 125
    Ile Thr Cys Lys Asp Met Arg Asn Leu Arg Phe Ala Leu Lys Gln Glu
            130                 135                 140
    Gly His Ser Arg Arg Asp Met Phe Glu Ile Leu Thr Arg Tyr Ala Phe
    145                 150                 155                 160
    Pro Leu Ala His Ser Leu Pro Leu Phe Ala Phe Leu Asn Glu Glu Lys
                    165                 170                 175
    Phe Asn Val Asp Gly Trp Thr Val Tyr Asn Pro Val Glu Glu Tyr Arg
                    180                 185                 190
    Arg Gln Gly Leu Pro Asn His His Trp Arg Ile Thr Phe Ile Asn Lys
                195                 200                 205
    Cys Tyr Glu Leu Cys Asp Thr Tyr Pro Ala Leu Leu Val Val Pro Tyr
            210                 215                 220
    Arg Ala Ser Asp Asp Leu Arg Arg Val Ala Thr Phe Arg Ser Arg
    225                 230                 235                 240
    Asn Arg Ile Pro Val Leu Ser Trp Ile His Pro Glu Asn Lys Thr Val
                    245                 250                 255
    Ile Val Arg Cys Ser Gln Pro Leu Val Gly Met Ser Gly Lys Arg Asn
                    260                 265                 270
    Lys Asp Asp Glu Lys Tyr Leu Asp Val Ile Arg Glu Thr Asn Lys Gln
                275                 280                 285
    Ile Ser Lys Leu Thr Ile Tyr Asp Ala Arg Pro Ser Val Asn Ala Val
            290                 295                 300
```

```
    Ala Asn Lys Ala Thr Gly Gly Gly Tyr Glu Ser Asp Asp Ala Tyr His
    305                 310                 315                 320
    Asn Ala Glu Leu Phe Phe Leu Asp Ile His Asn Ile His Val Met Arg
                    325                 330                 335
    Glu Ser Leu Lys Lys Val Lys Asp Ile Val Tyr Pro Asn Val Glu Glu
                340                 345                 350
    Ser His Trp Leu Ser Ser Leu Glu Ser Thr His Trp Leu Glu His Ile
                355                 360                 365
    Lys Leu Val Leu Thr Gly Ala Ile Gln Val Ala Asp Lys Val Ser Ser
    370                 375                 380
    Gly Lys Ser Ser Val Leu Val His Cys Ser Asp Gly Trp Asp Arg Thr
    385                 390                 395                 400
    Ala Gln Leu Thr Ser Leu Ala Met Leu Met Leu Asp Ser Phe Tyr Arg
                    405                 410                 415
    Ser Ile Glu Gly Phe Glu Ile Leu Val Gln Lys Glu Trp Ile Ser Phe
                420                 425                 430
    Gly His Lys Phe Ala Ser Arg Ile Gly His Gly Asp Lys Asn His Thr
                435                 440                 445
    Asp Ala Asp Arg Ser Pro Ile Phe Leu Gln Phe Ile Asp Cys Val Trp
    450                 455                 460
    Gln Met Ser Lys Gln Phe Pro Thr Ala Phe Glu Phe Asn Glu Gln Phe
    465                 470                 475                 480
    Leu Ile Ile Ile Leu Asp His Leu Tyr Ser Cys Arg Phe Gly Thr Phe
                    485                 490                 495
    Leu Phe Asn Cys Glu Ser Ala Arg Glu Arg Gln Lys Val Thr Glu Arg
                500                 505                 510
    Thr Val Ser Leu Trp Ser Leu Ile Asn Ser Asn Lys Glu Lys Phe Lys
                515                 520                 525
    Asn Pro Phe Tyr Thr Lys Glu Ile Asn Arg Val Leu Tyr Pro Val Ala
    530                 535                 540
    Ser Met Arg His Leu Glu Leu Trp Val Asn Tyr Tyr Ile Arg Trp Asn
    545                 550                 555                 560
    Pro Arg Ile Lys Gln Gln Pro Asn Pro Val Glu Gln Arg Tyr Met
                    565                 570                 575
    Glu Leu Leu Ala Leu Arg Asp Glu Tyr Ile Lys Arg Leu Glu Glu Leu
    580                 585                 590
    Gln Leu Ala Asn Ser Ala Lys Leu Ser Asp Pro Pro Thr Ser Pro Ser
                595                 600                 605
    Ser Pro Ser Gln Met Met Pro His Val Gln Thr His Phe
    610                 615                 620

<210> SEQ ID NO 9
<211> LENGTH: 771
<212> TYPE: PRT
<213> ORGANISM: C. elegans

<400> SEQUENCE: 9

Met Thr Val Thr Ser Ser Ala Ala Ile Asp Ile Gly Gly Gly Gly Gly
    1               5                   10                  15
    Gly Arg Arg Ser Asp Arg Leu Asp Ser Asp Arg Thr Ser Glu Asp Met
                    20                  25                  30
    Ser Phe Ile Ala Ser Pro Ala Asn Ile Gly Ala Ser Phe Val Asp Val
                35                  40                  45
    Gln Asn Glu Ser Ser Gly Ser Ile Asp Thr Ala Thr Ala Thr Leu His
    50                  55                  60
    Glu Leu Asn Tyr Thr Phe Gly Met Pro Pro Val Thr Glu Glu Ser Glu
    65                  70                  75                  80
    Asn Met Pro Gln Asn Tyr Glu Thr Val Val Glu Leu Leu Pro Gly Glu
                    85                  90                  95
    Glu Arg Ala Pro Ile Asn Lys Leu Thr Glu Phe Pro Ile Glu Gly Gly
                100                 105                 110
    Ser Leu Phe Val Thr Asn Phe Arg Ile Val Val Ile Leu Lys Asp Lys
                115                 120                 125
    Glu Val Glu Glu Ala Leu Arg Phe Leu Val Phe Pro Leu Gln Asp Ile
    130                 135                 140
    Glu Gln Ile Asp Leu Ala Ile Pro Ala Phe Ile His Leu Ser Leu Lys
    145                 150                 155                 160
    Ile Gly Arg Met Phe Thr Ile Cys Phe Lys Thr Ala Glu Asp Ala Ala
                    165                 170                 175
    Leu Val His Lys Ile Leu Tyr Thr Ala Phe Gln Arg Leu Asn Arg Pro
                180                 185                 190
    Ile Ser Ser Ile Tyr Thr Ser Arg Pro Gln Asp Trp Thr Ser Lys Asn
                195                 200                 205
    Thr Asp Asn Pro Met Gln Ser Leu Asn Ala Phe Ala Trp Lys Phe Ser
    210                 215                 220
    Glu Ala Val Asp Glu Leu Asp Arg Asp Gly Lys Leu Pro Ser Trp Leu
    225                 230                 235                 240
```

```
                Leu Arg Ala Asp Ser Val Ala Gln Glu Ile Thr His Ile Asp Phe Asn
                                245                 250                 255
                Arg Leu Gly Met Ser Glu His Phe Gln Ile Ser Ser Val Asn Glu Asn
                                260                 265                 270
                Phe Glu Val Cys Pro Thr Tyr Pro Glu Lys Ile Ile Val Pro Lys Gly
                                275                 280                 285
                Ile Thr Asp Asp Asp Ile Arg Lys Gly Ala Pro Tyr Arg Ser Ile Gly
                                290                 295                 300
                Arg Phe Pro Ala Val Ile Trp Arg Cys Arg Lys Thr Arg Ala Val Leu
                305                 310                 315                 320
                Met Arg Ser Ser Gln Pro Gln Val Gly Ile Leu Ser Trp Arg Asn Pro
                                325                 330                 335
                Thr Asp Glu Lys Ile Ile Glu Glu Ala Val Lys Ala Ser Arg Ile Glu
                                340                 345                 350
                Gly Glu Glu Lys Lys Gln Phe Ile Ile Met Asp Ala Arg Gly Tyr Thr
                                355                 360                 365
                Ser Ala Phe Ala Asn Arg Ala Arg Ser Gly Gly Phe Glu Asn Thr Glu
                                370                 375                 380
                Tyr Tyr Gln Gln Ala Lys Leu Glu Phe Leu Gly Leu Pro Asn Ile His
                385                 390                 395                 400
                Ala Val Arg Gly Ser Phe Asn Asn Val Arg Thr Met Leu His Asn Leu
                                405                 410                 415
                Gly Pro Asn Glu Gln Leu Leu Thr Ser Leu Gln Thr Thr Gly Trp Leu
                                420                 425                 430
                Leu Asn Leu Ser Asn Leu Leu Val Asn Ala Ala Asn Cys Ala Asp His
                                435                 440                 445
                Leu Ser Lys Gly His Ser Val Leu Val His Cys Ser Asp Gly Trp Asp
                450                 455                 460
                Arg Thr Thr Gln Val Thr Thr Leu Ala Lys Ile Met Leu Asp Glu Tyr
                465                 470                 475                 480
                Tyr Arg Thr Val Lys Gly Phe Glu Glu Leu Ile Arg Arg Asp Trp Ile
                                485                 490                 495
                Ala Phe Gly His Lys Leu Tyr Asp Arg Gln Leu Val Ala Phe Gly Asn
                                500                 505                 510
                Trp Gly Thr Ser Asp Glu Arg Ser Pro Val Phe Leu Gln Phe Leu Glu
                                515                 520                 525
                Ala Val Arg His Leu Gln Arg Glu Gln Pro Thr Leu Phe Gln Phe Thr
                                530                 535                 540
                His Ala Tyr Leu Ile Lys Leu Ala Lys His Ala Tyr Ser Gly Leu Phe
                545                 550                 555                 560
                Gly Ser Phe Leu Phe Asn Ser His Lys Glu Arg Arg Glu Ala Met Glu
                                565                 570                 575
                Lys Cys Lys Gly Thr Leu Val Asp Ile Trp Arg Phe Ile Gly Pro His
                                580                 585                 590
                Asn Glu Glu Tyr Val Asn Gln Ser Phe Asp Glu His Tyr Thr Gly Ala
                                595                 600                 605
                Val Lys Pro Gln Ile Phe Ser Pro Lys Glu Glu Arg Pro Leu Ser Gly
                                610                 615                 620
                Cys Thr Thr Pro Met Asn Thr Ser Thr Ser Thr Asn Leu Val Lys Ser
                625                 630                 635                 640
                Lys Ser Ser Glu Ser Ile Asn Ser Leu Asn Val Asp Gly Ser Ala Lys
                                645                 650                 655
                Glu Ser Ser Gln Gln His Pro Thr Cys Ser Thr Thr Pro Ser Asp Asn
                                660                 665                 670
                Thr Asn Ser Leu Pro Met Ser Thr Ser Phe Ile Gln Gln Ser Leu Tyr
                                675                 680                 685
                Gln Pro Lys Val Arg Gly Val Ala Ala Ile Asp Arg Asp Gly Val Ile
                                690                 695                 700
                Arg Phe Glu Asp Asp Glu Gln Ala Met Leu Arg Lys Lys Asn Lys Leu
                705                 710                 715                 720
                Arg Ala Glu Glu Ile Arg Arg Lys Asp Lys Ile Glu Glu Leu Arg
                                725                 730                 735
                Arg Arg Ala Val Leu Asp Thr Asn Lys Val Ser Pro Gly Gln Arg Gln
                                740                 745                 750
                Ser Tyr Ser Glu Ser Asp Val Glu Thr Thr Gly Thr Leu Glu Arg Val
                                755                 760                 765
                Met Ser Asp
                770
```